United States Patent [19]

Sigl

[11] Patent Number: 5,415,650
[45] Date of Patent: May 16, 1995

[54] ATTACHMENT SYSTEM AND METHOD OF ATTACHING AN ABSORBENT ARTICLE TO AN UNDERGARMENT

[75] Inventor: Wayne C. Sigl, Neenah, Wis.

[73] Assignee: Kimberly-Clark Corporation, Neenah, Wis.

[21] Appl. No.: 167,391

[22] Filed: Dec. 14, 1993

Related U.S. Application Data

[62] Division of Ser. No. 497,160, Mar. 20, 1990, abandoned.

[51] Int. Cl.⁶ .............................................. A61F 13/15
[52] U.S. Cl. .................... 604/387; 604/385.1; 604/389; 604/393; 604/397
[58] Field of Search ....................... 604/385.1-397

[56] References Cited

U.S. PATENT DOCUMENTS

| 2,890,701 | 6/1959 | Weinman | 128/291 |
|---|---|---|---|
| 2,949,114 | 8/1960 | De Woskin | 128/290 |
| 3,420,236 | 1/1969 | De Woskin | 128/291 |
| 3,460,535 | 7/1969 | Behna | 128/288 |
| 3,704,710 | 12/1972 | Fifer | 128/288 |
| 3,745,587 | 7/1973 | Bradley | 2/114 |
| 3,749,095 | 7/1973 | Toyama | 604/387 |
| 3,921,221 | 11/1975 | Zoephel | 2/51 |
| 4,040,124 | 8/1977 | Zoephel | 2/51 |
| 4,285,343 | 8/1981 | McNair | 128/287 |
| 4,342,808 | 8/1982 | Langen et al. | 428/194 |
| 4,522,874 | 6/1985 | Pommez | 428/284 |
| 4,578,073 | 3/1986 | Dysart et al. | 604/397 |
| 4,579,556 | 4/1986 | McFarland | 604/385 |
| 4,589,876 | 5/1986 | Van Tilburg | 604/385 R |
| 4,608,047 | 8/1986 | Mattingly | 604/387 |
| 4,609,373 | 9/1986 | Johnson | 604/389 |
| 4,687,478 | 8/1987 | Van Tilburg | 604/387 |
| 4,690,680 | 9/1987 | Higgins | 604/386 |
| 4,701,178 | 10/1987 | Glaug et al. | 604/387 |
| 4,832,742 | 5/1989 | Wilson et al. | 604/391 |
| 4,850,991 | 7/1989 | Nakanishi et al. | 604/387 |
| 4,959,265 | 9/1990 | Wood et al. | 428/343 |
| 5,085,655 | 2/1992 | Mann et al. | 604/389 |

Primary Examiner—Randall L. Green
Assistant Examiner—Rob Clarke
Attorney, Agent, or Firm—Mark L. Davis

[57] ABSTRACT

An attachment system and a method of attaching an absorbent article to an undergarment is disclosed. The attachment system includes an absorbent article having an absorbent, a liquid permeable cover and a liquid-permeable baffle. The cover and baffle cooperate to enclose the absorbent and form a pad having a garment facing surface, at least a portion of which is coated with a first cohesive-adhesive. The attachment system also includes an undergarment which is designed to be worn about the torso of a human body. The undergarment has a crotch portion which is at least partially coated with a second cohesive-adhesive. The absorbent article is positioned on and held secure to the crotch portion of the undergarment by cohering the first cohesive-adhesive to the second cohesive-adhesive.

13 Claims, 5 Drawing Sheets

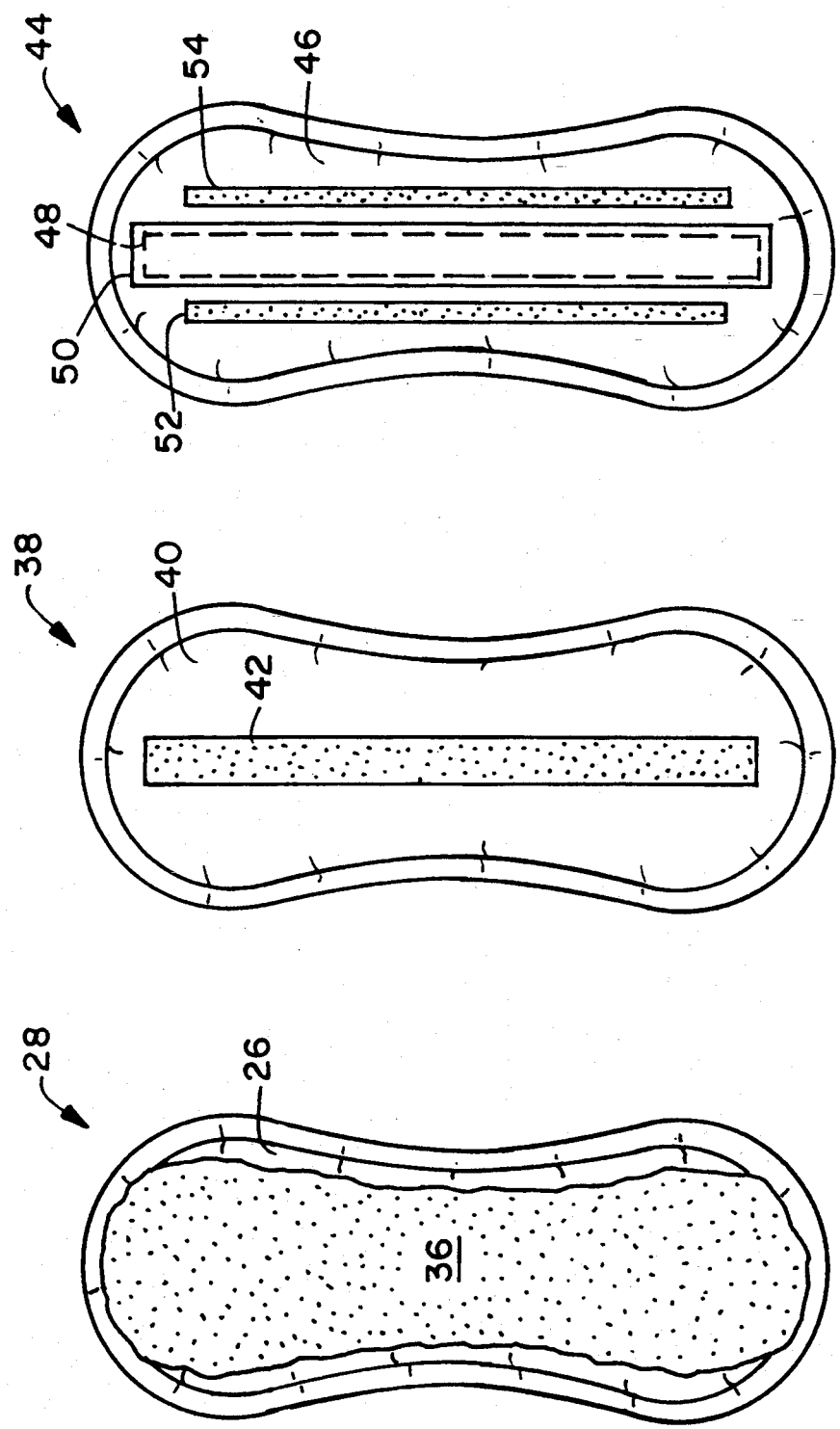

ATTACHMENT SYSTEM AND METHOD OF ATTACHING AN ABSORBENT ARTICLE TO AN UNDERGARMENT

This is a divisional application of application Ser. No. 07/497,160, filed on Mar. 20, 1990, now abandoned.

FIELD OF THE INVENTION

This invention relates to an attachment system and to a method of attaching an absorbent article, such as a feminine pad, to the crotch portion of an undergarment.

BACKGROUND OF THE INVENTION

Generally, absorbent articles like sanitary napkins, overnight pads, pantiliners, incontinent garments and even some underarm shields are designed to be attached to an adjacent garment, such as an undergarment, in order to hold the product stationary during use. Pressure-sensitive adhesives provide a common means of affixing a product to an adjacent garment. The pressure-sensitive adhesive can be designed to contact either the adjacent undergarment or the user's skin. One disadvantage of using pressure-sensitive adhesives is that the adhesive has to be covered by a releasable peel strip to prevent foreign matter from contaminating it prior to use. The peel strip increases the cost of the final product and the presence of the peel strip requires the end user to physically remove it before using the product. Representative samples of pressure-sensitive adhesive attachments can be found in U.S. Pat. Nos. 4,850,991; 4,701,178 and 4,690,680.

Other means of holding an absorbent article secure to an undergarment includes mechanical type fasteners. These include buttons and button holes, hooks and loops, and end extensions and tabs which are designed to interlock or engage some type of supporting belt or strap. These types of fasteners are being used less frequently today because most women find them difficult to attach and some are not very discrete under tight fitting clothing. Representative samples can be found in U.S. Pat. Nos. 4,609,373; 3,749,095; 3,704,710; 3,460,535; 3,420,236; 2,949,114 and 2,890,701.

Another approach to holding two members together is to utilize cohesive-adhesives. A cohesive-adhesive is a material which, after being coated or impregnated onto a surface, has an affinity for itself. Various compositions and types of cohesive-adhesives have been used on diapers, paper bags and hospital gowns to provide fastening means. U.S. Pat. Nos. 4,522,874; 4,342,808; 4,040,124; 3,921,221 and 3,745,587 teach some examples of how cohesive-adhesives can be used. However, none of the above prior art patents teach attachments of different disposable absorbent articles, each bearing a cohesive-adhesive surface, onto a reusable undergarment. The attachment of an absorbent article, by it's cohesive-adhesive, to the cohesive-adhesive coated onto the crotch portion of an undergarment ensures that the absorbent article will be held stationary relative to the undergarment.

Now an attachment system and method of attaching an absorbent article to an undergarment has been developed which will eliminate the use of pressure-sensitive adhesives and a releasable peel strip.

SUMMARY OF THE INVENTION

Briefly, the present invention relates to an attachment system and to a method of attaching an absorbent article, such as a feminine pad, to an undergarment. The attachment system includes an absorbent article having an absorbent, a liquid-permeable cover and a liquid-impermeable baffle. The cover and baffle cooperate to enclose the absorbent and form a pad having a garment facing surface, at least a portion of which is coated with a first cohesive-adhesive. The attachment system also includes an undergarment, which preferably, is designed to be worn about the torso of a human body. The undergarment has a crotch portion which is at least partially coated with a second cohesive-adhesive. The absorbent article is positioned on and held secure to the crotch portion of the undergarment by cohering the first cohesive-adhesive to the second cohesive-adhesive. It is contemplated that several feminine pads can be sequentially used in combination with a single pair of panties.

The method includes the steps of forming the absorbent article as described above and coating or impregnating at least a portion of the garment facing surface with a cohesive-adhesive. An undergarment is then formed and the crotch portion is coated or impregnated with a cohesive-adhesive. The absorbent article is positioned in the crotch portion of the undergarment and the cohesive-adhesives are brought into contact with one another to form a secure bond. However, the bond can be easily broken by removal of the original absorbent article and replacement of a new absorbent article is possible onto the original undergarment.

The general object of this invention is to provide an attachment system for securing an absorbent article, such as a feminine pad, to the crotch portion of an undergarment using cohesive-adhesives. A more specific object of this invention is to provide an attachment system for sequentially securing disposable feminine pads onto the crotch portion of a disposable or semi-disposable undergarment.

Another object of this invention is to provide a simple and easy method of attaching and removing a disposable sanitary napkin to and from the crotch portion of an undergarment.

Still, another object of this invention is to provide an attachment system for securing an absorbent article to an undergarment which does not utilize a pressure-sensitive adhesive in combination with a releasable peel strip.

Still further, an object of this invention is to provide an attachment system for securing a feminine pad to an undergarment which reduces the overall cost of the feminine pads and which is easy to apply.

Other objects and advantages of the present invention will become more apparent to those skilled in the art in view of the following description and the accompanying drawings.

BRIEF DESCRIPTION OF THE DRAWINGS

FIG. 3 is bottom view of absorbent article showing a cohesive-adhesive coated or impregnated onto essentially the entire surface.

FIG. 4 is a bottom view of an absorbent article showing a single, elongated strip of a cohesive-adhesive coated thereon.

FIG. 5 is a bottom view of an absorbent article showing a centrally located pressure-sensitive adhesive strip flanked by a pair of elongated cohesive-adhesive strips.

DETAILED DESCRIPTION OF THE PREFERRED EMBODIMENTS

Figure 1:
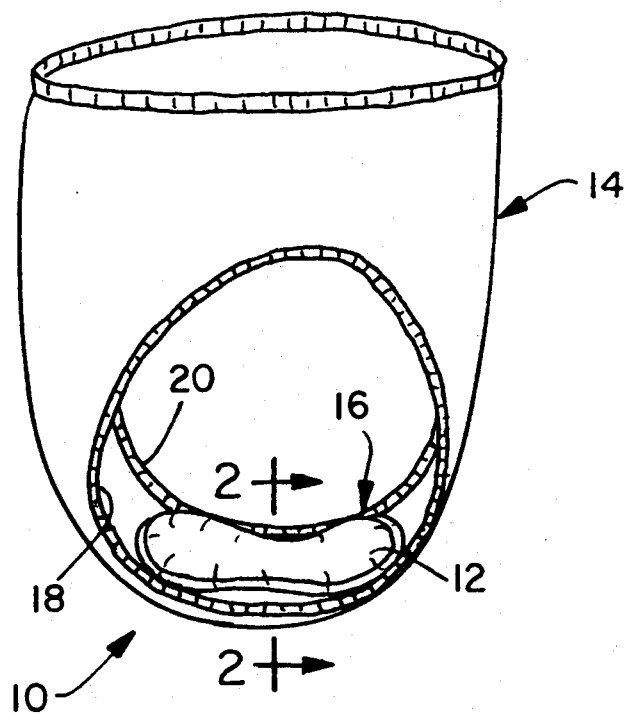
FIG. 1 is a perspective view of an undergarment designed to be worn about the torso of a human body and having an absorbent article, such as a sanitary napkin, positioned in the crotch portion thereof.

Referring to FIG. 1, an attachment system 10 is depicted for securing an absorbent article 12 to a garment 14. The absorbent article 12 can be a sanitary napkin, feminine pad, overnight pad, pantiliner, incontinent garment, underarm shield or even an insert style diapering product used to retain body fluids or waste. For discussion purposes only, the garment 14 is shown as an undergarment or panty designed to be worn about the torso of a human body. However, the garment 14 could be any type of underclothes, such as an undershirt, or it could be an exterior piece of clothing, for example a blouse which is used to hold an underarm shield in place. When the garment 14 is a pair of underwear or panty, it preferably will have a narrow crotch portion 16 located between two leg openings 18 and 20. The undergarment 14 can be made out of any woven or non-woven, elastic or non-elastic fabric material, provided the material can be coated, treated, or impregnated with an emulsion. Common materials include cotton cloth, nylon and polyester/cotton blends. Disposable and semi-disposable materials preferably include spunbonded polypropylene, spunbond/meltblown polypropylene laminates and other bonded carded webs utilizing fibers such as rayon, nylon, polyester, or blends thereof. Paper or treated paper can also be utilized. A spunbonded laminate is a particularly good material for making a ladies panties because it is thin, stretchable and discreet when worn.

The crotch portion 16 of the undergarment 14 can be made of the same material as the rest of the undergarment or it can be constructed of a different material. In either case, the crotch portion 16 should be porous and/or breathable. It is advantageous to make the crotch portion 16 out of an absorbent or hydrophilic material which has an affinity for water because this will provide comfort to the wearer in that it will not feel hot or sweaty while being worn. A hydrophilic material, or one that has been treated with a hydrophilic coating, will also be easier to coat or impregnate with a cohesive-adhesive emulsion. It should also be noted that it is possible to make the crotch portion 16 out of a perforated film material, although this is not preferred.

Figure 2:
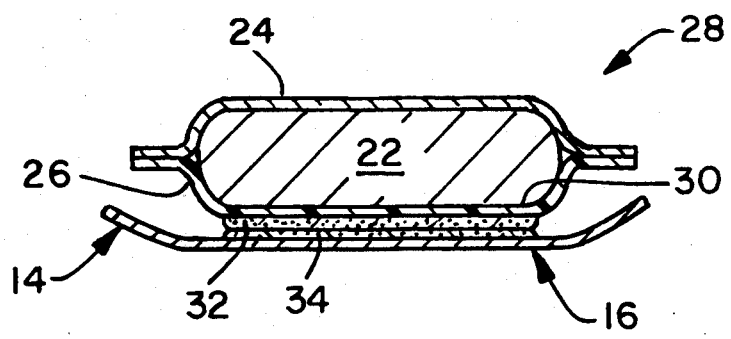
FIG. 2 is a cross-sectional view of the sanitary napkin shown in FIG. 1 taken along line 2—2.

Referring to FIG. 2, the absorbent article 12 contains an absorbent 22 enclosed or sandwiched between a liquid-permeable cover 24 and a liquid-impermeable baffle 26 to form a pad 28. It should be noted that the absorbent 22 can be affixed or be permanently attached to either the cover 24 or to the baffle 26 or to both if desired. The absorbent 22 is hydrophilic and can be made from cellulose fibers, wood pulp, regenerated cellulose or cotton fibers, or a blend of pulp and other fibers. Hydrocolloidal material, commonly referred to as superabsorbents, can also be added to the hydrophilic material to increase the absorption capacity. The cover 24 is designed to contact the wearer's body and can be constructed of a woven or non-woven, natural or synthetic material which is easily penetrated by body fluids. Thermoplastic polymer webs made from fibers or filaments of polyethylene or polypropylene are preferred. It is also beneficial to aperture the cover 24 to increase the rate at which the body fluids can penetrate down into the absorbent 22. The baffle 26 faces the inner surface of the undergarment 14 and is usually designed to permit the passage of air, or vapor to the outer surface while blocking the passage of fluids or liquids. The baffle 26 can be made from polymeric films such as polyethylene, polypropylene or cellophane, or be made from a bicomponent film. A preferred material is ethyl-vinyl-acetate/polyethylene coextruded film.

The baffle 26 has an exterior garment facing surface 30 which is treated, coated, impregnated or otherwise bears a first cohesive-adhesive 32. A cohesive-adhesive is a material which, after being attached to a surface or substrate and allowed to dry, has the unique property of having an affinity only for itself. Consequently, the cohesive-adhesive has little or no affinity for materials or surfaces which are not similar to itself. Most cohesive-adhesives can be considered to be inactive in bonding until placed in contact with a cohesive-adhesive of the same general type.

Generally, cohesive-adhesives suitable with this invention have a high shear adhesive-adherence and a low peel adhesive-adherence. The cohesive-adhesive can include aqueous emulsions or solvent solutions of rubber base adhesive, natural or synthetic, including crepe rubber and latex rubber. An eligible cohesive-adhesive for use in accordance with the present invention is sold under the trademark NIPWELD 207-939 and is manufactured by Findley Adhesives Inc. located at 11320 W. Watertown Plank Road, Milwaukee, Wis. 53226. Another suitable cohesive-adhesive is available from Industrial Adhesive Company located at 130 North Campbell Avenue, Chicago, Ill. 60612 and is sold under the product code L3108.

A suitable cohesive-adhesive is comprised of an aqueous ammoniacal emulsion having about 69 percent solids and about 0.003 percent ammonia. The solids are about 85 parts by weight polycisisoprene, originating from natural rubber, and about 15 parts by weight of vinyl acetate and n-butyl acrylate. Another suitable cohesive-adhesive composition and percentage is as follows:

| Percent (%) | |
| --- | --- |
| 74.00 | Natural Latex (62% solids) |
| 3.00 | Casein |
| 4.00 | Sodium Polyacrylate |
| 0.80 | Sodium Pentachlorophenate |
| 1.00 | 4,6 Dinonyl-O-Cresol |
| 0.01 | Toluene |
| 0.01 | Silicone Antifoam A (Dow Corning Co.) |
| 16.80 | Water |

The teaching in U.S. Pat. Nos. 4,522,874; 4,342,808 and 3,745,587 relating to cohesive-adhesives and the methods of applying them to a fabric are incorporated by reference and made a part hereof. It should also be noted that it is possible to produce a hot melt adhesive containing a ferro-magnetic substance. After the hot melt adhesive has been applied to a surface and allowed to dry, the surface is subjected to a magnetic field. The magnetic field causes the adhesive to become a cohesive-adhesive and will bond only to itself.

A second cohesive-adhesive 34 is applied to the crotch portion 16 of the undergarment 14. The second cohesive-adhesive 34 is designed to adhere or cohere, that is to stick, unite or cling, to the first cohesive-adhesive 32 when the two are brought into contact with one another. When the two cohesive-adhesives 32 and 34 cohere to one another, the absorbent article will be held secure to the adjacent garment. With feminine pads, it is common for a lady to position the pad in the narrow crotch portion of her undergarment and then pull the undergarment up around her torso. This same procedure can be followed with the present invention. The first and second cohesive-adhesives 32 and 34, respectfully, can be made from identical compositions or each can have a different composition provided each has an affinity for the other.

It is contemplated that several absorbent articles 12 can be packaged and sold in a cardboard box or plastic bag with one or more undergarments 14. The reason for this is that the cohesive-adhesive on the undergarment will allow for multiple attachments and removals of pads without losing its sticking power. It is also possible to sell the absorbent articles 12 and the undergarments 14 separately.

Both the first and second cohesive-adhesives 32 and 34, respectfully, can be coated or impregnated onto the undergarment 14 in a variety of ways. The cohesive-adhesive can be brushed on the fabric or the fabric can be submerged in a bath of the cohesive-adhesive material and thereafter pressed through rollers and dried. Other methods of applying the cohesive-adhesive include spraying, using a roller applicator wherein the roller contains holes through which the cohesive-adhesive may be fed under pressure or by gravity, or by silk screening. It has been found that the cohesive-adhesives 32 and 34 should have a thickness of less than 1 millimeter, and preferably, less than 0.5 millimeters when it is being applied to a sanitary napkin or undergarment.

Referring to FIGS. 3–5, three bottom views of feminine pads are depicted with various configurations of an applied cohesive-adhesive. In FIG. 3, the pad 28 contains a baffle 26 which is essentially completely coated or impregnated with a cohesive-adhesive 36. In FIG. 4, a pad 38 is shown having a baffle 40 containing a single, elongated strip of cohesive-adhesive 42. The strip 42 only partially covers the baffle 40 and is preferably located along the longitudinal central axis of the pad 38. The strip 42 has a length less than the overall length of the baffle 40 and is spaced apart from both ends of the pad 38. The length and width of the strip 42 can be varied to meet one's particular needs. In FIG. 5, a pad 44 is shown having a baffle 46 containing an elongated and centrally located, pressure-sensitive adhesive strip 48. This embodiment is useful when a person does not have a pair of panties which are coated with a cohesive-adhesive. The pressure-sensitive adhesive strip 48 is coaxially aligned with the longitudinal central axis of the pad 44 and is covered by a removable peel strip 50. The peel strip 50 is a thin sheet of paper which will prevent contamination of the adhesive 48 and is designed to be removed prior to use of the pad 44. A pair of cohesive-adhesive strips 52 and 54 are positioned adjacent to the pressure-sensitive adhesive 48. The two cohesive-adhesive strips 52 and 54 preferably cover or occupy a larger surface area of the baffle 46 than does the pressure-sensitive adhesive 48 because the cohesive-adhesive has less "sticking power" per square centimeter than the typical pressure-sensitive adhesive. The two cohesive-adhesive strips 52 and 54 can be sized and configured as desired. When the pressure-sensitive adhesive 48 is not to be utilized, the peel strip 50 can be left in place. Because of this option, the peel strip 50 should be sized and configured to be comfortable when brought in contact with the human body. For example, each corner of the peel strip 50 can be rounded and the edges can be made soft so as to eliminate discomfort.

Figure 6:
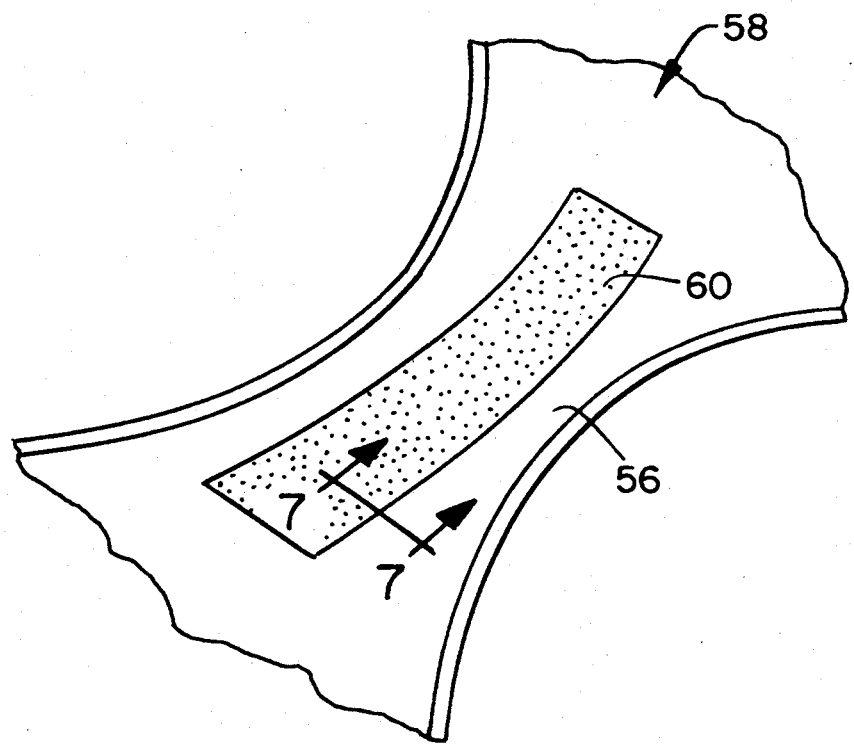
FIG. 6 is a partial view of the crotch portion of an undergarment having a cohesive-adhesive strip impregnated thereon.
Figure 7:
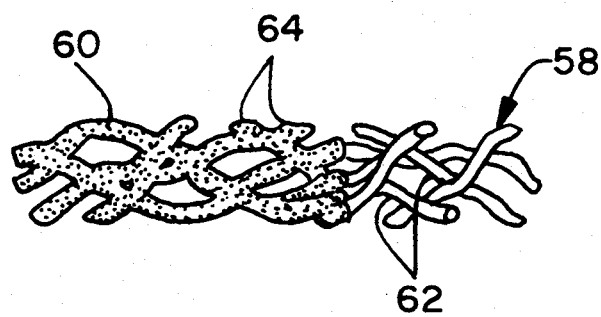
FIG. 7 is an enlarged cross-sectional view of FIG. 6 taken along line 7—7 showing the cohesive-adhesive impregnated on the surface of the fibers.

Referring to FIGS. 6 and 7, an undergarment 58 is shown having a cohesive-adhesive strip 60 impregnated onto the fibers 62 of the crotch portion 56. The entire outer surfaces 64 of the fibers 62 are covered by the cohesive-adhesive such that both the interior and exterior surfaces of the undergarment 58 exhibit the cohesive-adhesive. The ability to have the cohesive-adhesive impregnate the fibers and be exposed on both the inside and outside surfaces of the undergarment is beneficial when using a feminine pad having outwardly extending wings which are designed to wrap around the crotch portion of an undergarment.

Figure 8:
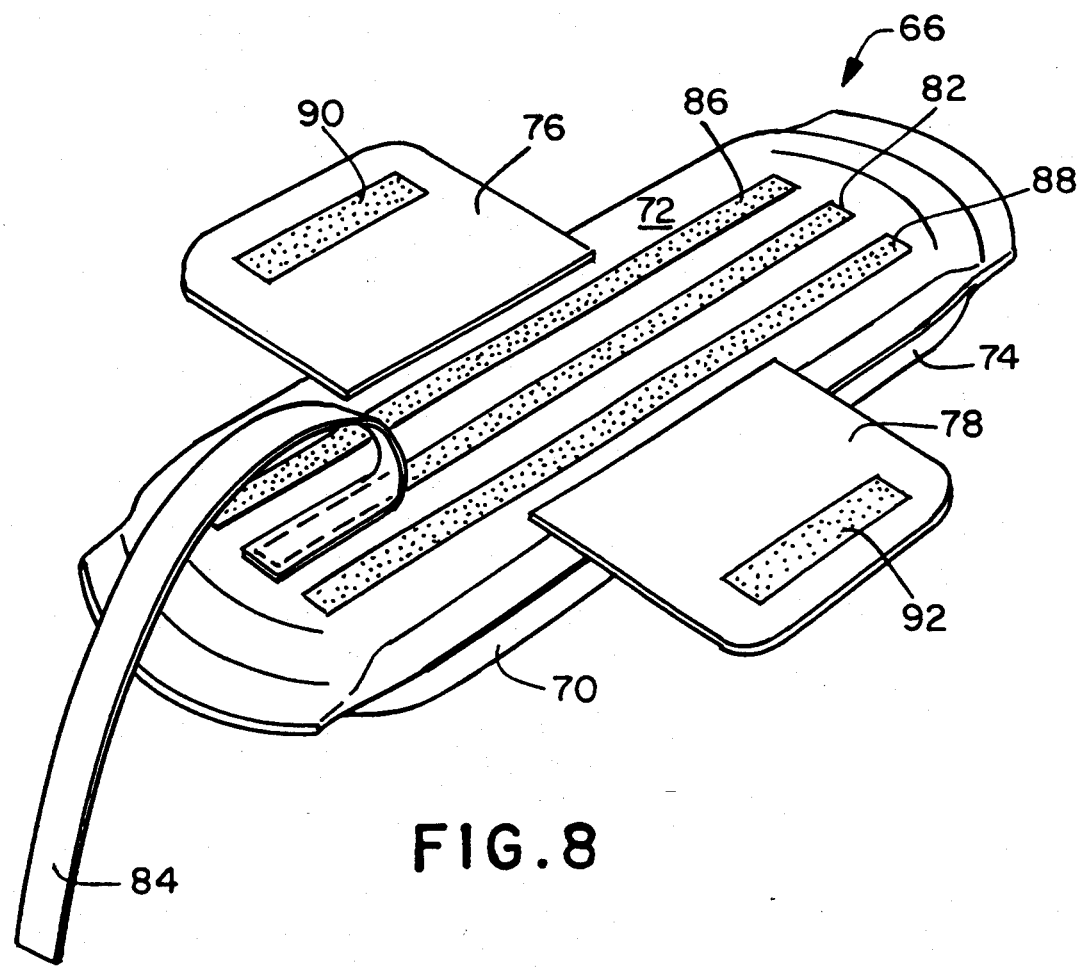
FIG. 8 is a perspective view of the underside of an absorbent article showing a central absorbent having a pressure-sensitive adhesive strip flanked by a pair of cohesive-adhesive strips and having a pair of outwardly extending wings each having a cohesive adhesive coating thereon.
Figure 9:
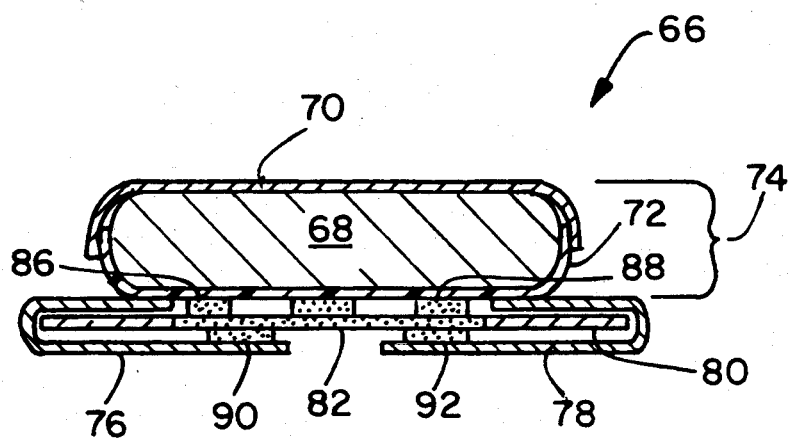
FIG. 9 is a cross-sectional view of the absorbent article shown in FIG. 8 when the wings are wrapped around the crotch portion of an undergarment.

Referring to FIGS. 8 and 9, a sanitary napkin 66 is depicted having an absorbent 68, a liquid permeable cover 70 and a liquid-impermeable baffle 72. The cover 70 and the baffle 72 cooperate to enclose the absorbent 68 and form a pad 74 having a pair of outwardly extending wings 76 and 78. The wings 76 and 78 are sized and configured to overlap at least a portion of the exterior surface of the crotch portion of an undergarment 80. It should be noted that the wings 76 and 78 can be an extension of the baffle 72 or be separate members attached to the baffle 72. The sanitary napkin 66 also contains a pressure-sensitive adhesive strip 82 secured to the baffle 72 and positioned along the longitudinal axis of the pad 74. A removable peel strip 84 covers the pressure-sensitive adhesive 82 until the sanitary napkin 66 is ready to be worn. As stated above, the presence of the pressure-sensitive adhesive strip 82 and the peel strip 84 are optional. A first pair of cohesive-adhesive strips 86 and 88 are secured to the baffle 72 approximate the outer edges of the pad 74. A second pair of cohesive-adhesive strips 90 and 92 are secured to the lower or bottom surface of the wings 76 and 78, respectfully. During application of the sanitary napkin 66 to the undergarment 80, the pad 74 is positioned onto the inner surface of the crotch portion and the wings 76 and 78 are wrapped around the crotch portion and cohere to the exterior surface of the undergarment, see FIG. 9. It should be noted that the undergarment 80 can be impregnated with a cohesive-adhesive strip, as shown in FIG. 6, or it can have a coating of cohesive-adhesive applied to both the inner and outer surfaces.

Figure 10:
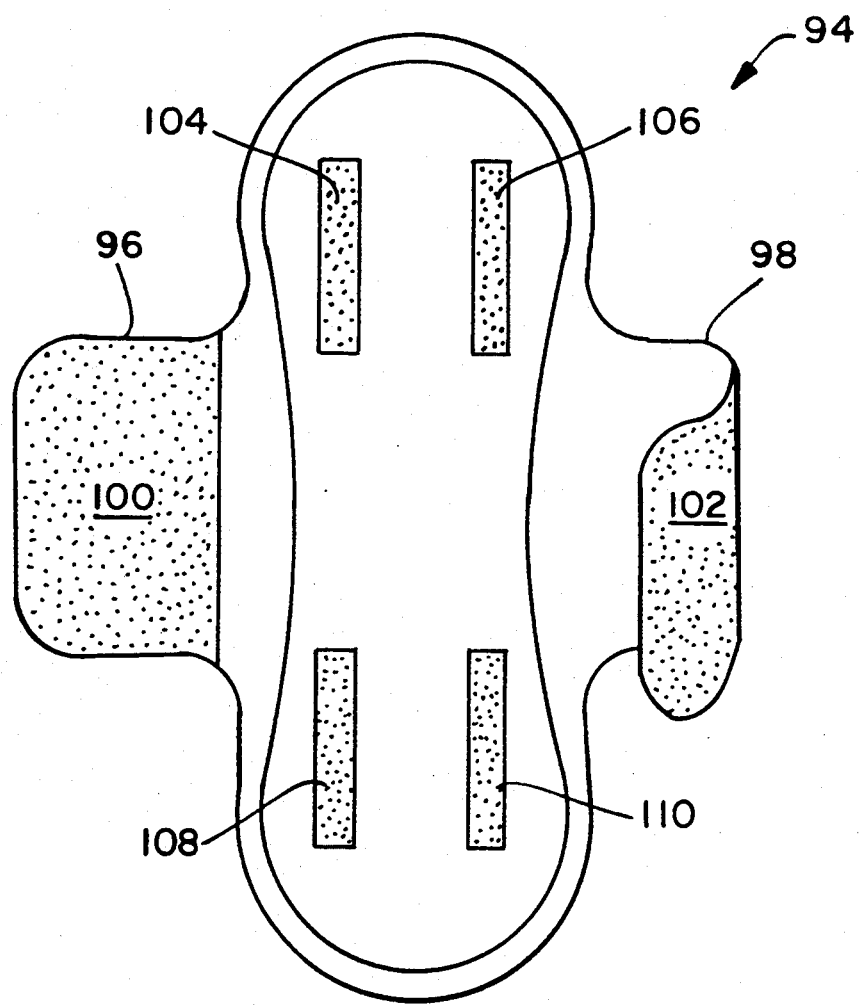
FIG. 10 is a bottom view of an absorbent article having a pair of laterally extending wings showing a cohesive-adhesive coated onto the garment facing surface of one wing and onto the opposite surface on the other wing.

Referring to FIG. 10, an alternative absorbent article 94 having a pair of wings 96 and 98 is shown. In this embodiment, one surface of each wing 96 and 98 is completely treated or covered with a cohesive-adhesive 100 and 102. The cohesive-adhesive 100 is coated on the garment facing surface of the wing 96 while the cohesive-adhesive 102 is coated on the upper surface of the wing 98. The wings 96 and 98 are sized to permit at least a portion of one wing to overlap a portion of the other wing and be fastened thereto. This embodiment permits the wings 96 and 98 to wrapped around the crotch portion of an undergarment and hold the absorbent article 94 in place without the need to coat the lower surface of the undergarment with a cohesive-adhesive. In addition, the absorbent article 94 contains four cohesive-adhesive strips 104, 106, 108 and 110 positioned between the two wings 96 and 98. It should be noted that even though four cohesive-adhesive strips are shown, the invention is not limited to this number and any number or plurality of strips or segments of cohesive-adhesive can be secured to the garment facing or lower surface of the article 94. The various arrangements of adhesives taught in U.S. Pat. Nos. 4,850,991 and 4,690,680 can be replaced with cohesive-adhesives or with a combination of cohesive-adhesives and pressure-sensitive adhesives. These two Pat. are incorporated by reference and made a part hereof.

Figure 11:
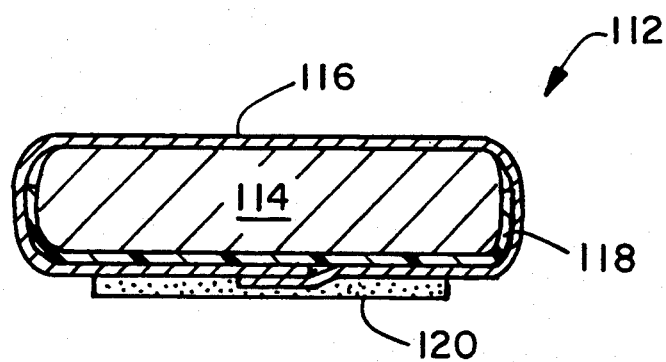
FIG. 11 is a cross-sectional view of an alternative embodiment of a sanitary napkin showing an absorbent and a baffle completely surrounded by a liquid permeable cover and having the cohesive-adhesive attached to the cover.

Referring to FIG. 11, an absorbent article 112 is shown comprised of an absorbent 114, a liquid-permeable cover 116 and a liquid-impermeable baffle 118. The baffle 118 is positioned adjacent to a surface of the absorbent 114 and the cover 116 completely encircles both the absorbent 114 and the baffle 118. The garment facing or lower surface of the cover 116 is coated with a cohesive-adhesive 120. This embodiment is shown to emphasize the fact that the cohesive-adhesive does not have to be coated directly onto the baffle.

Lastly, although the invention has been primarily described in relation to a feminine pad, it is envisioned to have other applications especially in diaper/insert type products and in panty/incontinent type products. U.S. Pat. Nos. 4,578,073 and 4,579,556 teach the use of pressure-sensitive adhesives to secure a disposable insert member to a reusable outer member. The cohesive-adhesive attachment system of this invention could be used to replace the standard adhesive.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. An attachment system comprising:
   a) an absorbent article having an absorbent, a liquid-permeable cover and a liquid-impermeable baffle, said cover and baffle cooperating to enclose said absorbent and form a pad having a garment facing surface, and a first cohesive-adhesive coated onto at least a portion of said garment facing surface said first cohesive-adhesive having a thickness of less than one millimeter; and
   b) a garment designed to be worn about the torso of a human body, said garment having a porous, nonelastic crotch portion wherein said crotch portion includes an interior surface disposed toward said absorbent and an exterior surface oppositely disposed, said surfaces having porous fibers which are at least partially impregnated with a second cohesive-adhesive, said absorbent article capable of being positioned on and held secure to said crotch portion of said garment by cohering said first cohesive-adhesive with said second cohesive-adhesive.

2. The attachment system of claim 1 wherein said porous fibers are coated with said second cohesive-adhesive.

3. The attachment system of claim 1 wherein said garment facing surface contains both a pressure-sensitive adhesive and a cohesive-adhesive.

4. The attachment system of claim 3 wherein said pressure-sensitive adhesive is covered by a releasable peel strip.

5. The attachment system of claim 1 wherein said cohesive-adhesive is an aqueous ammoniacal emulsion before being applied to said respected surface.

6. The attachment system of claim 1 wherein said absorbent article is a disposable insert member.

7. The attachment system of claim 3 wherein said pressure-sensitive adhesive is an elongated strip positioned along said longitudinal axis of said absorbent article and said first cohesive-adhesive is positioned on opposite sides thereof.

8. The attachment system of claim 7 wherein said cohesive-adhesive occupies a greater surface area than does said pressure-sensitive adhesive.

9. An attachment system comprising:
   a) an absorbent article having an absorbent, a liquid-permeable cover and a liquid-impermeable baffle, said cover and baffle cooperating to enclose said absorbent and form a pad having a pair of outwardly extending wings, said article further having a garment facing surface which is at least partially coated with a first cohesive-adhesive; and
   b) an undergarment designed to be worn about the torso of a human body, said undergarment having a porous, nonelastic crotch portion which is at least partially impregnated with a second cohesive-adhesive, said first and second cohesive-adhesive cohering to one another when brought into contact, said wings having a garment facing surface wherein said garment facing surface on one wing is coated with said first cohesive-adhesive and an upper surface on said other wing is coated with said first cohesive-adhesive, said wings being sized and configured to overlap at least a portion of said crotch portion whereby said absorbent article is held stationary relative to said undergarment.

10. The attachment system of claim 9 wherein said garment facing surface of each wing and an exterior surface of said crotch portion are covered with a first and a second cohesive-adhesive, respectively, and said first cohesive-adhesives present on said wings cohere to said second cohesive-adhesive present on said exterior surface of said crotch portion when they contact one another whereby said absorbent article is held secure to said undergarment.

11. A method of attaching an absorbent article to an undergarment, comprising the steps of:
   a) forming an absorbent article having an absorbent, a liquid-permeable cover and a liquid-impermeable baffle, said cover and baffle cooperating to enclose said absorbent to produce a pad having a garment facing surface;

b) coating at least a portion of said garment facing surface with a first cohesive-adhesive;

c) constructing an undergarment capable of being worn about the torso of a human body, said undergarment having a narrow, porous, nonelastic crotch portion;

d) impregnating at least a portion of said crotch portion with a second cohesive-adhesive; and e) positioning said pad within said undergarment with said garment facing surface aligned over said crotch portion and cohering said first and second cohesive-adhesives to secure said absorbent article to said undergarment.

12. The method of claim 11 wherein a surface of said baffle is coated with a cohesive-adhesive before said baffle is combined with said cover to enclose said absorbent.

13. A method of attaching an absorbent article to an undergarment, comprising the steps of:

a) forming an absorbent article having an absorbent, a liquid-permeable cover and a liquid-impermeable baffle, said cover and baffle cooperating to enclose said absorbent to produce a pad having a pair of outwardly extending wings, said wings being sized and configured to overlap at least a portion of a crotch portion of an undergarment, said pad further having a garment facing surface;

b) coating at least a portion of said garment facing surface with a first cohesive-adhesive;

c) constructing an undergarment capable of being worn about the torso of a human body, said undergarment having a narrow, porous, nonelastic crotch portion;

d) impregnating at least a portion of an exterior surface of said crotch portion with a second cohesive-adhesive; and e) positioning said pad within said crotch portion of said undergarment and folding said wings around at least a portion of said exterior surface of said crotch portion, and cohering said first and second cohesive-adhesives to secure said absorbent article to said undergarment.

* * * * *